US008431683B2

(12) United States Patent
Coszach et al.

(10) Patent No.: US 8,431,683 B2
(45) Date of Patent: Apr. 30, 2013

(54) CHEMICAL RECYCLING OF PLA BY HYDROLYSIS

(75) Inventors: Philippe Coszach, Escanaffles (BE); Jean-Christophe Bogaert, Escanaffles (BE); Jonathan Willocq, Saint-Sauveur (ES)

(73) Assignee: Galactic S.A., Escanaffles (BE)

( * ) Notice: Subject to any disclaimer, the term of this patent is extended or adjusted under 35 U.S.C. 154(b) by 0 days.

(21) Appl. No.: 13/263,198

(22) PCT Filed: Mar. 31, 2010

(86) PCT No.: PCT/EP2010/054274

§ 371 (c)(1), (2), (4) Date: Oct. 6, 2011

(87) PCT Pub. No.: WO2010/118954

PCT Pub. Date: Oct. 21, 2010

(65) Prior Publication Data

US 2012/0142958 A1 Jun. 7, 2012

(30) Foreign Application Priority Data

Apr. 14, 2009 (BE) .................................. 2009/0232

(51) Int. Cl.
*C08F 6/00* (2006.01)
*C08F 3/00* (2006.01)

(52) U.S. Cl.
USPC ........................................................ 528/480

(58) Field of Classification Search .................. 528/480
See application file for complete search history.

(56) References Cited

U.S. PATENT DOCUMENTS

| | | | | |
|---|---|---|---|---|
| 5,136,057 | A * | 8/1992 | Bhatia | 549/274 |
| 5,229,528 | A * | 7/1993 | Brake et al. | 549/274 |
| 5,264,614 | A | 11/1993 | Brake | |
| 5,264,617 | A | 11/1993 | Brake | |
| 2011/0160480 | A1 | 6/2011 | Hottois et al. | |

FOREIGN PATENT DOCUMENTS

| | | | |
|---|---|---|---|
| BE | 1017951 | A3 | 1/2010 |
| EP | 0628533 | A1 | 12/1994 |

OTHER PUBLICATIONS

International Search Report completed by the EP Searching Authority on May 20, 2010 in connection with PCT/EP2010/054274 (French text).
International Search Report completed by the EP Searching Authority on May 20, 2010 in connection with PCT/EP2010/054274 (English translation).
F.D. Kopinke, et al. "Thermal decomposition of biodegradable polyesters—II. Poly (lactic acid)", Polymer Degradation and Stability, vol. 53, 329-342, 1996.

* cited by examiner

*Primary Examiner* — Terressa Boykin
(74) *Attorney, Agent, or Firm* — Reichel IP LLP; Kevin R. Erdman; Mark C. Reichel

(57) ABSTRACT

A process for recycling a polymer blend necessarily containing PLA, comprising grinding, compacting, dissolving in a solvent of PLA, removing the undissolved contaminating polymers, hydroloysis depolymerization reaction and purification steps.

27 Claims, No Drawings

CHEMICAL RECYCLING OF PLA BY HYDROLYSIS

CROSS-REFERENCE TO RELATED APPLICATIONS

This application is the U.S. national phase of PCT/EP2010/054274 filed Mar. 31, 2010, the disclosure of which is incorporated by reference herein. PCT/EP2010/054274 claims the benefit under the Convention of Belgian Patent Application No. 2009/0232 filed Apr. 14, 2009, the disclosure of which is incorporated by reference herein.

FIELD OF THE INVENTION

The present invention relates to a process of chemical recycling also called depolymerisation of polylactide (PLA), whether contained or not in a blend of other polymers, for reforming the monomer or a derivative thereof.

Nowadays, in order to promote the extension of biopolymers, the use of which comes within the environment safety perspective, it is essential to be able to demonstrate the viability of management of the end-of-life of these products. The object of the present invention is to meet these issues in the case of polylactide (PLA) by providing an original solution different from the already existing ones.

STATE OF THE ART

The management of the end-of-life of plastic materials is a very important factor of the viability of a plastic material available on the market (for example, PVC has been taken off the market of plastic bottles for lack of an effective recycling system). Like non-renewable plastics (from petrochemistry) and even though their end-of-life channels are more numerous, biopolymers face technical challenges as far as this management of end-of-life is concerned. In particular, when very huge volumes are at stake, which are generated in goods market. It is the reason why it is important to address this problem.

Currently, different ways enabling to manage the end-of-life waste are already known such as dumping, incineration, composting, mechanical recycling or chemical recycling.

For the dumping, it has been seen that pollutants, mainly methane and carbon dioxide, but also pesticides, heavy metals and additives, are emitted upon degrading in a dump. If dumping waste has long been a practical and cheap solution, it has been observed, besides the above-mentioned pollutant emissions, that waste go on degrading producing leachates and gases which must continue to be discharged and processed for periods up to several tens of years. In the case of biopolymers, however, the pollution is less important since degradation products are less toxic. Nevertheless, the degradation duration sometimes long enough should be taken into consideration, which may be an issue when volumes to be processed are important.

The object of this invention is to reduce the waste volume by converting it into gases ($CO_2$, $H_2O$, $SO_x$, HCl, $NO_x$, . . . ), it is therefore unavoidable that the air composition in the vicinity of incinerators be altered and contains higher levels of toxic substances. In the case of bioplastics, $CO_2$ rejections are less of an issue because carbon is not a fossil origin, therefore the overall balance is neutral, or even slightly positive taking account of emissions due to the process (biomass towards bioplastics). On the contrary, other rejections are much of an issue and consequently unavoidably result in an altered air composition. If well designed and well operated, incinerators could reduce emissions thereof but this technology is extremely costly both in terms of investments and expenditures. However, incineration provides an alternative to dumping and enables producing energy, indeed, a boiler can recover heat and valorise it, possibly as electrical and thermal energy (cogeneration). Since incinerators were important sources of pollution in the past, they were called "thermal valorisation centres" and then "energy valorisation plants" in lieu of "incineration plants". However, files for implanting new units are increasingly complex to be managed because people who live in the surroundings do not accept to have an incinerator in the vicinity of their home any longer.

Biodegrability, an important property of biopolymers, can be advantageously valorised by composting which does not impact environment when necessary precautions are taken, nevertheless, the evolution of the start material to final stage depends on a great number of external factors (material dimensions, humidity rate, ventilation, pH, bacterial flora, carbon-nitrogen ratio, . . . ) sometimes restricting its use. Moreover, the difficulty in identifying and sorting products containing biodegradable polymers (food packages, bags, . . . ) may deteriorate the compost quality in the case a mistake upon sorting is made. Besides, improving PLA quality (better thermal resistance, better mechanical properties, . . . ) results in a slower degradation.

Mechanical recycling is also known and used, for example in the case of poly(ethylene terephthalate) (PET). It consists in remelting the material, alone or in admixture with virgin material, to make marketable products. Waste is washed, dried, crystallised and ground and then directly transformed into finished products or granules which may then be marketed. This pathway is also applicable to PLA. However, since the temperatures used are high, a polymer degradation is often observed, involving a loss of its mechanical properties, both for PLA and any other polymers. The product can then be directed to less noble applications or be mixed with virgin materials. Therefore, this type of recycling is not infinite. Moreover, recycling poses problems when plastics are of different compositions since they generally are not compatible between one other. Indeed, the transformation temperatures are different and mixing several plastics results in a decrease of the quality of mechanical characteristics of the final product.

These different end-of-life techniques are not ideal because the plastic materials are not recycled into base elements (monomers) and thus directly and perpetually usable. Yet, these processes are viable for PLA but only if the material flow is exclusively comprised of PLA. Indeed, if other polymers contaminate PLA, the different above-mentioned techniques are made difficult. For example, in the case of a PET contamination, the latter is not degraded in a compost. In the case of a PVC contamination, incineration is possible but involves using costly filters due to noxious releases. Regarding chemical recycling, the obtained product is completely denatured if it is comprised of a polymer blend.

Another recycling pathway is also known as chemical recycling. Often quoted as the ideal recycling pathway, it consists in transforming the polymer by a chemical process such as for example: thermal or catalytic cracking into hydrocarbons, pyrolysis which converts back to monomers, . . . . A chemical recycling system for PET is known, that is depolymerisation thereof by a diol, also called glycolysis. The molecular chain is broken and the obtained products are terephthalic acid and ethylene glycol. Nevertheless, some degradation mechanisms during this depolymerisation generate irreversible structural modifications of the material, which can be responsible for difficulties in successive transformations. A PLA chemical recycling system may also be contemplated in order to recover the monomer, lactic acid or a derivative thereof. Some patents claim for example fast hydrolysis (Brake, L. D.; Subramanian, N. S. U.S. Pat. No. 5,229,528, 1993) or solvolysis (Brake, L. D. U.S. Pat. No. 5,264,614, 1993; Brake, L. D. U.S. Pat. No. 5,264,617, 1993) of a poly(hydroxy-acid) including PLA while producing hydroxy-acids or esters thereof. These known processes even enable to achieve a yield close to 95% but this involves performing a great number of steps (esterification followed by distillation, these steps being repeated three times). However, it turns out that such a handling has a serious caking risk in particular during distillation steps, which makes a transposition of the process at the industrial scale uncertain. It also turns out that dissolving the alcohol is not an easy task. Indeed, in the case of ethanol for example, it is not possible to continuously add (and thus at atmospheric pressure) PLA at a temperature higher than 78° C. (boiling point of ethanol). Due to the low density of some non densified homogenates, this results in a restricted PLA concentration. Besides, the PLA feeding the chemical recycling flow generally contains water in low amounts. This water can cause a hydrolysis of the ester formed, which can release lactic acid this way. This lactic acid production is very cumbersome in the case where the aimed quality involves a purification through distillation with rectification following solvolysis. Indeed, the distillation could not be conducted optimally, since the presence of lactic acid promotes an oligomerisation of the medium (BE Patent BE 20080424 "Procédé continu d'obtention d'un ester lactique"). Thermal degradations (for example pyrolysis) of PLA are also known, causing lactide formation (F. D. Kopinke, M. Remmler, K. Mackenzie, M. Möder, O. Wachsen, Polymer Degradation and stability, 53, 329-342, 1996) through an addition-elimination cyclization mechanism. But these methods have a low monomer yield. Moreover, these different techniques are often carried out at high temperature and/or high pressure which causes a chemical and optical degradation of the lactic acid obtained.

Therefore, there is a need for a simple, effective and non-denaturating process for depolymerising PLA in order to be able to recycle it as the basis monomer or one derivative thereof.

BRIEF DESCRIPTION OF THE INVENTION

One object of the present invention is to provide a process for the chemical recycling or depolymerisation of PLA, whether contained or not in a blend of other polymers, into lactic acid or a derivative thereof, such as a lactic acid salt, through hydrolysis, under mild conditions, by producing monomers with high quality and high yield, by increasing productivity, by decreasing $CO_2$ emissions and reducing the energy cost.

Another object of the invention is to dissolve PLA in a PLA solvent which does not block its depolymerisation and which does not impose further purification steps.

One further object of the present invention is to provide a process for the chemical recycling of a polymer blend necessarily containing PLA, wherein the blend is dissolved in a solvent for PLA to first separate the solid impurities such as polymers other than PLA which are not dissolved, and then the PLA solution is subjected to hydrolysis in order to transform PLA into the monomer or a derivative thereof.

One object of the process of the present invention is also to use as a solvent for dissolving PLA, a lactic ester so as to highly simplify the process, as well as having a positive impact on all the steps of the process for the chemical recycling of polylactic acid.

DETAILED DESCRIPTION OF THE INVENTION

The applicant has found that performing such a depolymerisation process could be remarkably improved if dissolving PLA or a polymer blend containing PLA in a lactic ester was carried out beforehand.

The process of the invention comprises consecutively the following steps; first grinding PLA or a polymer blend containing PLA is carried out, a lactic ester is used for dissolving PLA and simultaneously separating solid impurities such as polymers other than PLA which are undissolved, and then the solution thus obtained is subjected to a depolymerisation through hydrolysis and finally the lactic acid or a derivative thereof obtained is purified so as to obtain products meeting specific demands of the conventional market such as industrial applications or even PLA polymerisation.

1. Grinding the PLA Waste

Within the scope of the present invention, the raw materials used during this chemical recycling may come from out of specification products in production units, production trimmings in transformation units as well as finished products at the end of their life. First, grinding PLA or a polymer blend containing PLA is carried out according to either technique known to those skilled in the art, as for example shearing, impact, dry or water grinding. Since the object of this step is to increase the specific surface area of materials, so as to obtain a weight/volume ratio between 0.05 and 1.4 t/m$^3$, which enables to make handling steps easier and speed up the following dissolving step, making the process more easily industrializable. Within the scope of the invention, one or more grinding steps can be contemplated, their number depending on the starting product but also on the cost of these operations and the targeted final granulation. It is also possible to pre- or post-process PLA flows or polymer blend containing PLA in particular by proceeding to a washing with water or other solutions such as for example soda, potash or detergent solution, . . . . Other conducting, such as manual sorting or an automatic (for example magnetic) separation can be contemplated, all this for the purpose of remove possible waste which could alter the quality of the final product or complicate purification thereof. It is also obvious that if the waste from PLA or the polymer blend containing PLA to be processed have a suitable surface area to start dissolving, this grinding step may be suppressed without departing from the process of the present invention.

Following this grinding step, when performed, a densification step may be contemplated in order to compact the material, which would improve the handling and logistics steps.

2. Dissolving PLA or the Polymer Blend Containing Ground PLA

Then, the polymer blend containing PLA, whether ground or not, and compacted or not, is dissolved prior to the depolymerisation step. The dissolving can also be carried out without prior grinding if the form of PLA or the polymer blend containing PLA (weight/volume ratio) permits it. Indeed, one of the problems for processing this type of flow is the difference in specific mass of the different reprocessed materials event after the grinding step. Even though it is known that a main advantage of this dissolving is to remove the problem of the low density of the material to be processed (even when an identification step is carried out), thus resulting in an improved productivity per volume unit. Furthermore, the solvent used must not be cumbersome for subsequent steps.

First, this enables to easily separate the polymers other than PLA and to recover them for a specific, separated and subsequent processing.

Various solvents are known to dissolve PLA such as benzene, toluene, isopropyl ether, dichloromethane, chloroform, chlorobenzene, and so on. Even though these solvents are perfectly able to be suitable to perform dissolving PLA, they are nevertheless not recommended in view of the ecological background aimed at in this case.

Surprisingly, it has now be found that by carrying out this dissolving of PLA in a lactic acid ester, the further subsequent separation step could be avoided without decreasing the recycled or depolymerised material yield. These are esters such as methyl lactate, ethyl lactate, isopropyl lactate, butyl lactate, hexyl lactate, . . . and more generally a lactic acid alkyl ester, the alkyl radical of which has from 1 to 12 carbon atoms. It has also been found that dissolving lactic ester has the advantage to be able to be carried out at higher temperatures than those reached during the solubilisation in the alcohol this ester is derived of. Indeed, the boiling temperature of the ester is generally higher than that of the alcohol, which enables dissolving more PLA. Moreover, this dissolving is fast enough and is carried out quite rapidly.

The applicant has now found that it is possible through this handling to double the PLA volume capacity and thus the amount of processed material. This dissolving may be prior or simultaneous to the following step and carried out at different temperatures up to the PLA melting temperature.

In the case of a PLA flow contamination by another polymer (PET, PE, PVC, PP or any other common polymers), it is possible to remove the latter through filtration or any other means known to those skilled in the art.

Indeed, lactic esters do no enable dissolving the above-mentioned polymers for the required processing times.

3. The Chemical Recycling of PLA

After this dissolving, the following step consists in depolymerising PLA in order to convert it back to its basis monomer (lactic acid) or one derivative thereof. It is preferable to carry out this operation under sufficiently mild conditions to avoid a degradation of the lactic acid or one derivative thereof. Providing dissolved PLA enables the imperative obligation to exceed its melting temperature to be avoided and thus due to milder conditions, the degradation reactions to be reduced and thus to allow for obtaining a yield close to 100%.

The applicant company has also shown that PLA depolymerisation could be made through hydrolysis at a temperature between 80 and 180° C., preferably between 100 and 150° C., and more preferably between 120 and 140° C., under depression or at a pressure between the atmospheric pressure and 10 bars or higher. This hydrolysis step enables lactic acid or a salt thereof to be formed. It is implemented by breaking down an ester linkage of the polymer chain followed by a nucleophilic attack. This nucleophilic attack can be carried out using water or an alkaline solution such as NaOH, KOH, and so on. Since the amount of water or alkaline solution influences the reaction kinetics, it is nevertheless important to hold a compromise enabling removing too high an amount of water to be avoided during the subsequent purification steps. The hydrolysis can be carried out using or not (autocatalysed reaction) a Lewis acid type acidic catalyst such as for example tin octoate, tin lactate, antimony octoate, zinc octoate, APTS (para-toluene sulfonic acid), etc. or basic, of the Guanidines family, such as for example TBD (triazabicyclodecene) and derivatives thereof.

4. The Hydrolysis of the Lactic Acid Ester

According to the process of the invention, it can be also contemplated to hydrolyse the lactic acid ester used for dissolving PLA. This reaction is then carried out with addition of water or not in the presence or the absence of the catalyst, whether or not bonded on a resin. Preferably, this will be bonded. The amount of water recommended will be minimum for a maximum yield, in order to decrease the energy expenditure during the concentration of the lactic acid obtained. This hydrolysis can be carried out at atmospheric pressure or under depression, it can also be conducted in a batch or continuous manner by any method known to those skilled in the art such as reactive distillation, use of a piston flow reactor, . . . . The reaction is:

Lactic acid ester+water ⇔ lactic acid+alcohol

It is necessary to carry out the extraction of alcohol in order to shift the equilibrium of the reaction towards the formation of lactic acid.

The recovered lactic acid meets specifications of industrial applications or other from the market. In some cases, it could be used for reforming PLA.

5. The Purification of the Lactic Acid Ester Obtained through Hydrolysis

This part of the invention consists in purifying the lactic acid obtained during PLA hydrolysis, since the product purity may be variable depending on the use being aimed at. It is possible to achieve high quality grades meeting market criteria. Any purification technique known to those skilled in the art which generally comprises common steps such as removal of ions (ion exchange resins, liquid/liquid extraction, . . . ), removal of colour and other impurities (filtration, active carbon, and so on), concentration, distillation (rectification, thin layer, and so on) but also crystallization, etc. can be contemplated. Since the hydrolysis is carried out at a lower temperature, the product degradation is lesser, which makes the purification step easier.

With this process, it is thus possible to form a "loop" PLA→lactic acid→PLA, involving a lower carbon footprint than that of biomass (biomass→lactic acid→PLA→biomass).

Other details and features of the invention, given herein below by way of non-limiting examples, appear more clearly from the description as some possible embodiments.

Example 1

Recycling a PLA Fibre by Dissolving in a Lactic Ester Followed by an Hydrolysis 3.000 kg of PLA fibres have been ground using a knife grinder. This homogenate has then been dissolved in 2.000 kg of LEt in a vitrified reactor. The dissolving has been carried out at 130° c. at atmospheric pressure. Once the dissolving has ended, 2.250 kg of demineralised water have been added. The contents of the reactor are then heated until a pressure of 2.4 bars is obtained. The temperature achieved during the reaction is 137° C. Since this is lower than the PLA melting temperature, this thus avoids a degradation of the material. The products resulting from the hydrolysis, as well as their respective contents are set out in Table 1. The entire PLA has been converted into lactic acid. Surprisingly, the ethyl lactate has only been slightly hydrolysed.

TABLE 1

| Characteristics of the hydrolysate | | | |
|---|---|---|---|
| Lactic acid[(a)] (%) | Water[(b)] (%) | LEt[(c)] (%) | Ethanol[(c)] (%) |
| 56.0 | 21.0 | 22.1 | 0.9 |

[(a)]determined by titration
[(b)]determined by Karl Fischer measurement
[(c)]determined by ethyl lactate GC The obtained lactic acid has been purified through crystallization. In a reactor, 2 kg of lactic acid have been heated at 40° C. under stirring. Then, 0.4 g of a suspension containing crystals has been added. The lactic acid is then cooled from 40 to 30° C. in a few hours. The suspension is then centrifuged and the formed crystals recovered. The purity of the recovered product is of the heat stable grade.

This way of performing enables in a single reaction step and a simple purification, to recover 97% of lactic acid with respect to 100% theoretically expected on the basis of the PLA initially introduced.

Example 2

Dissolving in a Lactic Ester

Within the scope of this example, ground PLA has been dissolved in different lactic acid esters, that is methyl lactate, ethyl lactate and n-butyl lactate, in an oven at 130° C., at atmospheric pressure and without stirring. The results of these dissolvings are set out in Table 2.

TABLE 2

| Dissolving PLA in different lactic acid esters | | | | |
|---|---|---|---|---|
| test | Ester | PLA/ester mass ratio | time (hr) | Complete dissolving |
| 1 | methyl L | 1 | 1.5 | yes |
| 2 | ethyl L | 1 | 2 | yes |
| 3 | n-butyl L | 1 | 3 | yes |

The solubilisation at atmospheric pressure of PLA in the lactic esters or their respective alcohols has been compared in the following example.

TABLE 3

| Comparison of the dissolvings of PLA in lactic esters or their respective alcohols | | | | | |
|---|---|---|---|---|---|
| test | Solvent | PLA/ester mass ratio | Temp. (° C.) | time (hr) | Complete dissolving |
| 1 | Ethanol | 1 | 78° C. | 3 | no |
| 2 | ethyl L | 1 | 120° C. | 3 | yes |
| 3 | n-butanol | 1 | 120° C. | 3 | no |
| 4 | n-butyl L | 1 | 120° C. | 3 | yes |

In the case of ethyl lactate, different ester/PLA ratios and different temperatures have been studied and compared after a 4 hrs duration without stirring at atmospheric pressure. The results are set out in Table 4.

TABLE 4

| Dissolving in ethyl lactate of ground PLA in different proportions | | | |
|---|---|---|---|
| test | PLA/LEt mass ratio | t (° C.) | Dissolving at |
| 1 | 0.75 | 130 | 100% |
| 2 | 1 | 130 | 100% |
| 3 | 1.5 | 130 | 100% |
| 4 | 2 | 130 | 100% |
| 5 | 1 | 120 | 100% |
| 6 | 1.25 | 120 | 100% |
| 7 | 1.5 | 120 | 100% |
| 8 | 1.75 | 120 | ~85% |
| 9 | 2 | 120 | ~75% |

Tests 8 and 9 have been continued for 2 further hours. The entire PLA test 8 is dissolved. Conversely, 10% of the PLA from test 9 have not been dissolved.

A dissolving of ground fibres (density=0.22) has been carried out under conditions close to industrial ones (stirring, higher quantities of material, at atmospheric pressure, . . . ). 1.5 kg of PLA has been dissolved in 1 kg of ethyl lactate at 130° C. The end of dissolving is observed 5 minutes after the last addition. The obtained solution had a density of about 1.25.

It also has been attempted to dissolve different polymers likely to be able to contaminate the PLA flow, in ethyl lactate, at 130° C., at atmospheric pressure, for 4 hrs and without stirring. The results are set out in Table 5.

TABLE 5

| Dissolving in ethyl lactate of different ground polymers | | | |
|---|---|---|---|
| Polymer | Polymer/LEt mass ratio | Dissolving | Appearance of the blend |
| PEHD | 1 | no | suspension |
| PP | 0.14 | no | suspension |
| PET | 0.37 | no | suspension |
| PLA* | 1 | yes | solution |

*given by way of comparative example

The previous example seems to prove that separating polymers contaminating the PLA by dissolving in a lactic acid ester is possible. For this to be confirmed, dissolvings in ethyl lactate, of PLA contaminated by one of these polymers (10%) have been carried out at 130° C., for 4 hrs and without stirring (polymer/LEt mass ratio=0.5). The insolubles are then recovered by filtration, and then thoroughly washed with water, dried and weighed. The results are set out in Table 6. The slight differences in masses before and after dissolving attempt are due to the accuracy of the method being used.

TABLE 6

| Dissolving in ethyl lactate of PLA contaminated by another polymer | | | |
|---|---|---|---|
| Test | Polymer tested | Amount of contaminant before dissolving | Amount of contaminant recovered |
| 1 | PEHD | 2.03 g | 2.04 g |
| 2 | PP | 1.99 g | 1.99 g |
| 3 | PET | 2.04 g | 2.03 g |

Example 3

Hydrolysis of Ground PLA in the Presence of NaOH

In a 2 liter flask, 600 g of ground PLA and 400 g of ethyl lactate are added in order to dissolve the PLA. Then, 938 g of 50% NaOH are added by small fractions to the PLA dissolved avoiding to raise to a temperature higher than 90° C. The reaction lasted 24 hr at atmospheric pressure. The recovered hydrolysate is then filtered and analysed. The sodium lactate content is 64.5%, which represents a PLA and LEt hydrolysis yield of more than 95%.

Example 4

Dissolving Ground PLA Contaminated with Poly(Ethylene Terephthalate) (2%) in Ethyl Lactate Followed by the Hydrolysis Reaction in the Presence of Water—Removal of PET after Dissolving 3,000 kg of ground PLA cups have been contaminated with 2% poly(ethylene terephthalate), that is 60 g. The polymer blend has then been dissolved in 2,000 kg of LEt in a vitrified reactor. The dissolving has been carried out at 130° C., at atmospheric pressure and under stirring. The solution has then been filtered while hot in order to recover the undissolved PET. This operation enables to recover the entire contaminating polymer (that is 24 g).

The filtrate has been decanted in a vitrified reactor and 2,250 kg of demineralised water have been added. The contents of the reactor are then heated until a pressure of 2.4 bars is obtained. The temperature achieved during the reaction is 135° C. This is lower than the PLA melting temperatures. The hydrolysate has been analysed and the results are set out in Table 7. The entire PLA has been converted into lactic acid. The ethyl lactate has been slightly hydrolysed.

TABLE 7

| Characteristics of the hydrolysate | | | |
|---|---|---|---|
| Lactic acid[(a)] (%) | Water[(b)] (%) | LEt[(c)] (%) | Ethanol[(c)] (%) |
| 54.2 | 20.6 | 23.4 | 1.8 |

[(a)]determined by titration
[(b)]determined by Karl Fischer measurement
[(c)]determined by ethyl lactate GC The obtained solution has then been concentrated through evaporation of the volatile compounds (ethanol, water and ethyl lactate). The lactic acid has then been distilled off. This way of performing enables in a single reaction step and a simple purification, to recover 97% of lactic acid with respect to 100% theoretically expected on the basis of the initially introduced PLA and the partially hydrolysed lactic ester.

Example 5

Dissolving Ground PLA Contaminated with Polypropylene (1%) in Ethyl Lactate Followed by the Hydrolysis Reaction in the Presence of Water—Removal of PP after Reaction 3,000 kg of ground PLA cups have been contaminated with 2% polypropylene, that is 30 g. The polymer blend has then been dissolved in 2,000 kg of LEt in a vitrified reactor. The dissolving has been carried out at 130° C. at atmospheric pressure. Once the dissolving has ended, 2,250 kg of demineralised water have been added. The contents of the reactor are then heated until a pressure of 2.4 bars is obtained. The temperature achieved during the reaction is 136° C. This is lower than the PLA and PP melting temperatures. The recovered hydrolysate is then filtered. The 30 g of polypropylene have been completely recovered. The filtrate has been analysed and the results are set out in Table 8. The entire PLA has been converted into lactic acid. The ethyl lactate has been slightly hydrolysed.

TABLE 8

| Characteristics of the hydrolysate after filtration | | | |
|---|---|---|---|
| Lactic acid[(a)] (%) | Eau[(b)] (%) | LEt[(c)] (%) | Ethanol[(c)] (%) |
| 55.9 | 19.9 | 22.1 | 2.1 |

(d): determined by titration
(e): determined by Karl Fischer measurement
[(a)]determined by ethyl lactate GC The obtained solution has then been concentrated through evaporation of the volatile compounds (ethanol, water and ethyl lactate). The lactic acid has then been distilled off. This way of performing enables in a single reaction step and a simple purification, to recover 98% of lactic acid with respect to 100% theoretically expected on the basis of the initially introduced PLA and the partially hydrolysed lactic ester.

The invention claimed is:

1. A process for recycling a polymer blend comprising PLA, comprising the steps of:

a) dissolving said polymer blend in a solvent of PLA in order to separate PLA from the other polymers;

b) recovering undissolved polymers for separate and subsequent processing;

c) recovering the PLA solution with a weight ratio PLA/solvent between about 0.5 and about 3.0 and subjecting it to a catalytic hydrolysis reaction, at a temperature between about 80° C. and about 180° C. and a pressure between about 0.05 and about 10 bars, in order to transform PLA into lactic acid or a derivative thereof; and d) purifying the lactic acid or derivative thereof thus recovered.

2. The process according to claim 1, wherein said solvent of PLA is selected from benzene, toluene, isopropyl ether, dichloromethane, chloroform, chlorobenzene or lactic acid ester.

3. The process according to claim 2, wherein dissolving the polymer blend in a lactic acid ester is carried out at a temperature between 80° C. and the boiling temperature of the ester at operating pressure, for a period of time sufficient to obtain a weight ratio of PLA/lactic ester between about 0.5 and about 3.0.

4. The process according to claim 1, wherein the operating pressure is between about 0.05 and about 10 bars.

5. The process according to claim 2, characterised in that the lactic acid ester is an alkyl lactate, wherein the alkyl radical of the alkyl lactate contains from 1 to 12 carbon atoms.

6. The process according to claim 5, wherein the radical of the alkyl lactate is selected from the group consisting of methyl, ethyl, isopropyl, butyl or hexyl lactate.

7. A process for recycling PLA by depolymerising the PLA into a monomer or a derivative thereof, comprising dissolving PLA in a solvent, catalytically hydrolysing the dissolved PLA into lactic acid or a derivative thereof, and purifying the lactic acid or derivative thereof thus recovered, wherein dissolving PLA is performed at a temperature between 80° C. and the boiling temperature of the solvent at the operating pressure for a period of time sufficient to obtain a weight ratio of PLA/ester solvent between about 0.5 and about 3.0.

8. The process according to claim 7, characterised in that the operating pressure is between about 0.05 and about 10 bars.

9. The process according to claim 7, wherein said solvent of PLA is selected from benzene, toluene, isopropyl ether, dichloromethane, chloroform, chlorobenzene or lactic acid ester.

10. The process according to claim 9, wherein the lactic acid ester is an alkyl lactate, wherein the alkyl radical of the alkyl lactate contains from 1 to 12 carbon atoms.

11. The process according to claim 10 wherein the alkyl radical of the alkyl lactate is selected from the group consisting of methyl, ethyl, isopropyl, butyl or hexyl lactate.

12. The process according to claim 2 wherein said solvent of PLA is lactic acid ester.

13. The process according to claim 12, characterised in that the weight ratio of PLA/lactic acid ester is between about 0.75 and about 2.0.

14. The process according to claim 1, characterised in that the catalytic hydrolysis reaction is performed in the presence of an acidic catalyst.

15. The process according to claim 1, characterised in that the catalytic hydrolysis reaction is performed in the presence of a basic catalyst.

16. The process according to claim 7, characterized in that the weight ratio of PLA/lactic acid ester is between about 0.75 and about 2.0.

17. The process according to claim 7, characterised in that the catalytic hydrolysis reaction is performed in the presence of an acidic catalyst.

18. The process according to claim 7, characterised in that the catalytic hydrolysis reaction is performed in the presence of a basic catalyst.

19. A process for recovering lactic acid, characterised in that it comprises the steps of:

a) dissolving said polymer blend in a solvent of PLA in order to separate PLA from the other polymers;
b) recovering undissolved polymers for separate and subsequent processing;
c) recovering the PLA solution with a weight ratio PLA/solvent between about 0.5 and about 3.0 and subjecting it to a catalytic hydrolysis reaction, at a temperature between about 80° C. and about 180° C. and a pressure between about 0.05 and about 10 bars, in order to transform PLA into lactic acid or a derivative thereof;
d) purifying the lactic acid or derivative thereof thus recovered; and
e) hydrolyzing the lactic acid ester into lactic acid.

20. The process according to claim 19, characterised in that the hydrolysis of the lactic acid ester into lactic acid is performed in the presence of a catalyst.

21. The process according to claim 19, characterised in that the hydrolysis of the lactic acid ester into lactic acid is carried out at atmospheric pressure.

22. The process according to claim 19, characterised in that the hydrolysis of the lactic acid ester into lactic acid is carried out using reactive distillation.

23. The process according to claim 19, characterised in that the hydrolysis of the lactic acid ester into lactic acid is performed via extraction of alcohol.

24. The process according to claim 9, wherein said solvent of PLA is lactic acid ester.

25. The process according to claim 1, wherein said polymer blend is grinded and/or compacted to a weight ratio between 0.05 and 1.4 t/$m^3$ prior to dissolving.

26. The process according to claim 7, wherein said polymer blend is grinded and/or compacted to a weight ratio between 0.05 and 1.4 t/$m^3$ prior to dissolving.

27. The process according to claim 19, wherein said polymer blend is grinded and/or compacted to a weight ratio between 0.05 and 1.4 t/$m^3$ prior to dissolving.

* * * * *